(12) United States Patent
Linden et al.

(10) Patent No.: US 7,041,471 B1
(45) Date of Patent: May 9, 2006

(54) CAROTENE HYDROXYLASE AND METHOD FOR PRODUCING XANTHOPHYLL DERIVATIVES

(75) Inventors: Hartmut Linden, Constance (DE); Gerhard Sandmann, Offenbach (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/958,380

(22) PCT Filed: Mar. 28, 2000

(86) PCT No.: PCT/EP00/02711

§ 371 (c)(1),
(2), (4) Date: Jan. 22, 2002

(87) PCT Pub. No.: WO00/61764

PCT Pub. Date: Oct. 19, 2000

(30) Foreign Application Priority Data

Apr. 9, 1999 (DE) ................ 199 16 140

(51) Int. Cl.
*C12P 23/00* (2006.01)
*C12N 9/02* (2006.01)
*C07H 21/04* (2006.01)

(52) U.S. Cl. ............... 435/67; 435/189; 435/468; 435/471; 435/252.3; 435/252.33; 435/254.11; 435/410; 435/320.1; 435/67; 536/23.2

(58) Field of Classification Search .......... 435/189, 435/252.33, 410, 320.1, 67; 536/23.2, 23.1
See application file for complete search history.

(56) References Cited

FOREIGN PATENT DOCUMENTS

| EP | 393 650 | 10/1990 |
|---|---|---|
| EP | 735 137 | 10/1996 |
| EP | 747 483 | 12/1996 |
| WO | 91/13078 | 9/1991 |
| WO | 97/36998 | 10/1997 |
| WO | 99/07867 | 2/1999 |

OTHER PUBLICATIONS

J.Bacteriology, vol. 172, Dec. 1990 No. 12, 6704-6712, Misawa et al.
PlantcellPhysio. 39(5) :560-564 (1998), Masamoto et al.
J. Bacteriology, vol. 177, No. 22, 1995, 6575-6584, Misawa et al.
J. Bio.Chem., vol. 272, No. 10, Mar. 1997, 6128-6135, Fraser et al.
Pat.Abst.Japan, vol. 199, No. 5, 11-046770.
J.Sci, Ind, Res., vol. 57, Feb. 1998, 51-63, Krishna et al.
Biochimica et Biophysical, 1446 (1999) 203-212 ,Linden,H.

*Primary Examiner*—Nashaat T. Nashed
(74) *Attorney, Agent, or Firm*—Novak Druce & Quigg LLP

(57) ABSTRACT

The present invention relates to proteins which have an enzymatic activity for converting β-carotene into zeaxanthin or canthaxanthin into astaxanthin, to nucleic acids which encode these proteins, to nucleic acid constructs comprising these nucleic acids, to genetically manipulated organisms where the genetic manipulation causes or increases the gene expression of this nucleic acid by comparison with a wild-type, and to processes for preparing xanthophyll derivatives.

10 Claims, 2 Drawing Sheets

US 7,041,471 B1

CAROTENE HYDROXYLASE AND METHOD FOR PRODUCING XANTHOPHYLL DERIVATIVES

BACKGROUND OF THE INVENTION

The present invention relates to proteins which have an enzymatic activity for converting β-carotene into zeaxanthin or canthaxanthin into astaxanthin, to nucleic acids which encode these proteins, to nucleic acid constructs comprising these nucleic acids, to genetically manipulated organisms where the genetic manipulation causes or increases the gene expression of this nucleic acid by comparison with a wild-type, and to processes for preparing xanthophyll derivatives.

Xanthophylls are oxygen-containing carotenoids of animal, plant or microbial origin. Xanthophylls such as lutein, zeaxanthin or astaxanthin are important additives in the human and livestock diet as pigmenting substances and precursors of vitamin A derivatives. In addition, xanthophylls have a health-promoting action such as enhancing the immune response and, by reason of their antioxidant properties, a cancer-preventing action, which makes their use as nutraceuticals of interest. An economic process for preparing xanthophylls and foodstuffs with an increased xanthophyll content are therefore of great importance. Particularly economic processes for preparing xanthophylls are biotechnological processes which make use of proteins and biosynthesis genes of xanthophyll biosynthesis from xanthophyll-producing organisms.

Prokaryotic β-carotene hydroxylases which catalyze the enzymatic conversion of β-carotene into zeaxanthin via β-cryptoxanthin, and the genes which encode these proteins are known from the bacteria *Erwinia uredovora* (Misawa et al., J. of Bacteriology 1990, 6704–6712; EP 393690 B1), *Erwinia herbicola* (WO 9113078), *Agrobacterium aurantiacum* (Misawa et al., J. of Bacteriology 1995, 6575–6584; EP 735 137 A1), *Alcaligenes* sp. PC-1 (EP 735 137 A1), *Flavobacterium* sp. strain R1534 (Pasamontes et al., Gene 1997, 185, 35–41; EP 747483 A2) and from the *Cyanobacterium Synechocystis* sp. PCC6803 (Masamoto et al., Plant Cell Physiol. 1998, 39(5), 560–564).

It is also known that the prokaryotic β-carotene hydroxylases from *Agrobacterium aurantiacum, Alcaligenes* and *Erwinia uredovora* are additionally able to covert canthaxanthin via adonirubin in astaxanthin (Misawa et al., J. of Bacteriology 1995, 6575–6584; Fraser et al., J. Biol. Chem. 1997, 272, 6128–6135).

From eukaryotic sources, three plant β-carotene hydroxylases are known to catalyze the enzymatic conversion of β-carotene into zeaxanthin via β-cryptoxanthin. The corresponding cDNAs have been isolated from *Arabidopsis thaliana* (Cunningham et al, J. Biol. Chem. 1996, 271, 24349–24352, WO 9736998), and from *Capsicum an-nuum* L. (Bouvier et al., Biochimica et Biophysica Acta 1998, 1391, 320–328).

Genes of eukaryotic origin have the advantage over prokaryotic genes that they are expressed better in higher transgenic organisms such as plants. Nevertheless, there is still a need to improve and increase the xanthophyll productivity for an economic process for preparing xanthophyll derivatives or foodstuffs with an increased xanthophyll content by incorporating eukaryotic nucleic acids into organisms.

In addition, the appropriate eukaryotic β-carotene hydroxylases in the prior art have the disadvantage that they have only a narrow substrate range so that there is a build up of metabolic products which cannot be converted by the hydroxylases and may exert an inhibiting effect on the hydroxylases.

BRIEF SUMMARY OF THE INVENTION

It is an object of the present invention to remedy the described deficiencies of the prior art and to provide a eukaryotic β-carotene hydroxylase with improved properties.

We have found that this object is achieved by a protein which has an enzymatic activity for converting β-carotene into zeaxanthin or canthaxanthin into astaxanthin, comprising the amino acid sequence SEQ ID NO. 2 or a sequence derived from this sequence by substitution, insertion or deletion of amino acids and having a homology of at least 50% at the amino acid level with the sequence SEQ ID NO.2.

DETAILED DESCRIPTION OF THE INVENTION

Figure 1:
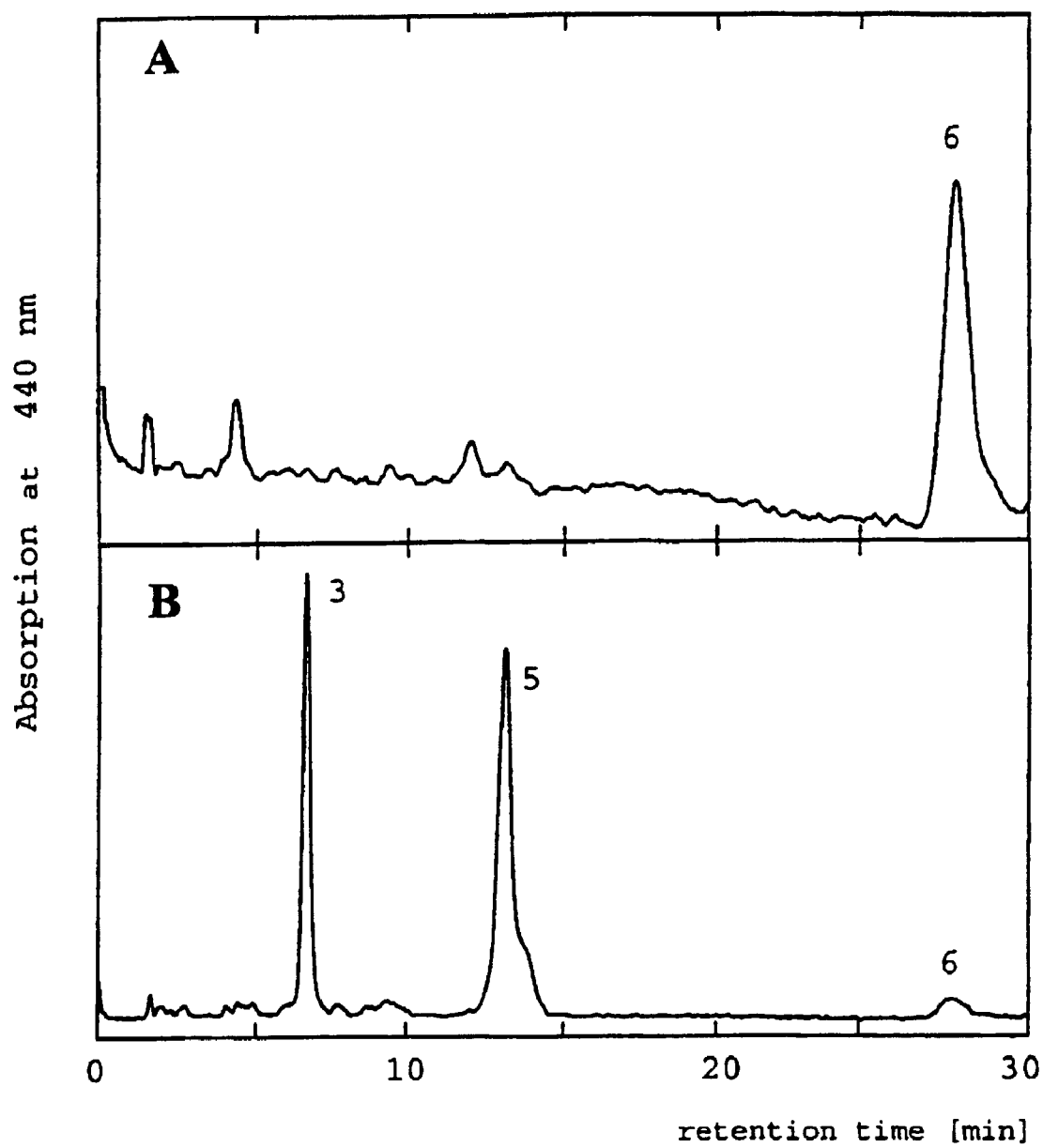
FIG. 1 shows the HPLC diagram for the carotenoids extracted from (A) *E. coli* cells containing the plasmid pACCAR16DcrtX, and (B) *E. coli* cells containing the plasmid pACCAR16DcrtX together with the carotene hydroxylase gene.

Carotene hydroxylases hereinafter mean the proteins according to the invention, i.e. proteins which have an enzymatic activity for converting β-carotene into zeaxanthin or canthaxanthin into astaxanthin, comprising the amino acid sequence SEQ ID NO. 2 or a sequence derived from this sequence by substitution, insertion or deletion of amino acids and having a homology of at least 50% at the amino acid level with the sequence SEQ ID NO.2.

The amino acid sequence depicted in SEQ ID NO. 2 is derived from translation of the cDNA sequence depicted in SEQ ID NO. 1.

The proteins according to the invention are able to catalyze the conversion of a β-ionone structural element into a 3-hydroxy-β-ionone structural element, such as the conversion of β-carotene into zeaxanthin, β-carotene into β-cryptoxanthin, β-cryptoxanthin into zeaxanthin, echinenone into 3'-hydroxyechinenone, 3-hydroxyechinenone into adonixanthin (4-ketozeaxanthin), α-carotene into α-cryptoxanthin or other chemical compounds which have up to 40 C atoms and contain a β-ionone ring into the corresponding 3-hydroxy-β-ionone compounds or the conversion of a 4-keto-β-ionone structural element into a 3-hydroxy-4-keto-β-ionone structural element, such as the conversion of canthaxanthin into astaxanthin, canthaxanthin into phoenicoxanthin (adonirubin), phoenicoxanthin (adonirubin) into astaxanthin, echinenone into 3-hydroxyechinenone, 3'-hydroxyechinenone into adonixanthin (4-ketozeaxanthin) or other chemical compounds which have up to 40 C atoms and contain a 4-keto-β-ionone ring into the corresponding 3-hydroxy-4-keto-β-ionone compounds.

For illustration of the xanthophylls derived from β-carotene, reference is made to the biosynthesis scheme in Misawa et al., J. Biotechnol. 1998, 59, page 174 (top). The biosynthesis of lutein takes place starting from α-carotene via α-cryptoxanthin. The proteins which comprise a sequence which is derived from amino acid sequence SEQ ID NO. 2 by substitution, insertion or deletion of amino acids and which have an homology of at least 50% at the amino acid level with the sequence SEQ ID NO.2 have an enzymatic activity for the conversion of β-carotene into zeaxanthin or canthaxanthin into astaxanthin, preferably in an activity comparable to that of the protein comprising the sequence SEQ ID NO. 2.

Substitution means replacement of one or more amino acids by one or more amino acids. The replacements are preferably those called conservative, in which the replaced amino acid has a similar property to the original amino acid, for example replacement of Glu by Asp, Gln via Asn, Val by Ile, Leu by Ile, Ser by Thr.

Deletion is the replacement of an amino acid by a direct linkage. Preferred positions for deletions are the termini of the polypeptide and the linkages between the individual protein domains.

Insertions are introductions of amino acids into the polypeptide chain, there formally being replacement of a direct linkage by one or more amino acids.

The homology between two proteins means identity of the amino acids over the entire length of each protein, which is calculated by comparison with the aid of the computer program GAP (UWGCG, University of Wisconsin, Genetic Computer Group, program algorithm of Needleman and Wunsch, J. Mol. Biol. 1970, 48, 443–453), setting the following parameters:

| | |
|---|---|
| Gap Weight: | 12 |
| Length Weight: | 4 |
| Average Match: | 2.912 |
| Average Mismatch: | −2.003 |

A protein which has a homology of at least 50% at the amino acid level with the sequence of SEQ ID NO.2 accordingly means a protein which, in comparison of its sequence with the sequence SEQ ID NO.2 using the above program algorithm with the above set of parameters, has an identity of at least 50%, preferably 60%, particularly preferably 70%.

The carotene hydroxylase according to the invention has a homology with the known prokaryotic β-carotene hydroxylases of 29.9% (*Flavobacterium*), 36.8% (*Erwinia uredovora*), 38.5% (*Erwinia herbicola*), 35.0% (*Alcaligenes*) and 35.6% (*Agrobacterium aurantiacum*), and a homology of 41.2% with the known eukaryotic β-carotene hydroxylase from *Arabidopsis thaliana*.

A preferred protein has an enzymatic activity for the conversion of β-carotene into zeaxanthin and an enzymatic activity for the conversion of canthaxanthin into astaxanthin and comprises the amino acid sequence SEQ ID NO. 2 or a protein which is derived from this sequence by substitution, insertion or deletion of amino acids and which has a homology of at least 50% at the amino acid level with the sequence of SEQ ID NO.2.

These preferred proteins are able to catalyze the conversion of a β-ionone structural element into a 3-hydroxy-β-ionone structural element, such as the conversion of β-carotene into zeaxanthin, β-carotene into β-cryptoxanthin, β-cryptoxanthin into zeaxanthin, echinenone into 3'-hydroxyechinenone, 3-hydroxyechinenone into adonixanthin (4-ketozeaxanthin), α-carotene into α-cryptoxanthin or other chemical compounds which have up to 40 C atoms and contain a β-ionone ring into the corresponding 3-hydroxy-β-ionone compounds and the conversion of a 4-keto-β-ionone structural element into a 3-hydroxy-4-keto-β-ionone structural element, such as the conversion of canthaxanthin into astaxanthin, canthaxanthin into phoenicoxanthin (adonirubin), phoenicoxanthin (adonirubin) into astaxanthin, echinenone into 3-hydroxyechinenone, 3'-hydroxyechinenone into adonixanthin (4-ketozeaxanthin) or other chemical compounds which have up to 40 C atoms and contain a 4-keto-β-ionone ring into the corresponding 3-hydroxy-4-keto-β-ionone compounds.

A particularly preferred protein is the eucaryotic carotene hydroxylase from the green alga *Haematococcus pluvialis* Flotow NIES-144 having the sequence SEQ ID NO. 2. This particularly preferred protein is able to catalyze the conversion of a β-ionone structural element into a 3-hydroxy-β-ionone structural element, such as the conversion of β-carotene into zeaxanthin, β-carotene into β-cryptoxanthin, β-cryptoxanthin into zeaxanthin, echinenone into 3'-hydroxyechinenone, 3-hydroxyechinenone into adonixanthin (4-ketozeaxanthin), α-carotene into α-cryptoxanthin or other chemical compounds which have up to 40 C atoms and contain a β-ionone ring into the corresponding 3-hydroxy-β-ionone compounds and the conversion of a 4-keto-β-ionone structural element into a 3-hydroxy-4-keto-α-ionone structural element, such as the conversion of canthaxanthin into astaxanthin, canthaxanthin into phoenicoxanthin (adonirubin), phoenicoxanthin (adonirubin) into astaxanthin, echinenone into 3-hydroxyechinenone, 3'-hydroxyechinenone into adonixanthin (4-ketozeaxanthin) or other chemical compounds which have up to 40 C atoms and contain a 4-keto-β-ionone ring into the corresponding 3-hydroxy-4-keto-β-ionone compounds.

The carotene hydroxylases can be prepared, as described hereinafter, by gene expression of the appropriate nucleic acids which encode these proteins from natural or genetically manipulated organisms.

The invention further relates to nucleic acids, referred to as carotene hydroxylase genes hereinafter, which encode the proteins according to the invention described above. Suitable nucleic acid sequences can be obtained by back-translation of the polypeptide sequence in accordance with the genetic code. The codons preferably used for this purpose are those frequently used in accordance with the organism-specific codon usage. The codon usage can easily be found by means of computer analyses of other, known genes in the relevant organism.

If, for example, the protein is to be expressed in a plant, it is often advantageous to use the codon usage of the plant in the back-translation.

A preferred nucleic acid has the sequence SEQ ID NO. 1. This nucleic acid is a eucaryotic cDNA from the green alga *Haematococcus pluvialis* Flotow NIES-144, which encodes the carotene hydroxylase of sequence SEQ ID NO. 2. Since the reading frame of the cDNA is open toward the 5' end, SEQ ID NO. 1 possibly does not represent the complete sequence of the cDNA. Expression of this cDNA leads to a functional protein. Any partial sequence missing out the 5' end can be made up in a manner known per se by analyzing overlapping cDNA fragments of the cDNA library from *Haematococcus pluvialis* Flotow NIES-144.

It is known that the green alga *Haematococcus pluvialis* produces large amounts of astaxanthin under unfavorable environmental conditions such as a phosphate or nitrogen deficit or where the light intensity is high, to protect from photooxidative stress (Kobayashi et al., Appl. Environ. Microbiol. 1993, 59, 867–873; Boussiba et al., Methods Enzymol 1992, 213, 386–391). This process is normally accompanied by a morphological change in which the vegetative cells of the green algae develop into cyst cells.

Addition of sodium acetate and $FeSO_4$ and an increase in the light intensity induced astaxanthinbiosynthesis and cyst cell formation in a suspension culture of *Haematococcus pluvialis* Flotow NIES-144. The RNA was isolated from *Haematococcus pluvialis* in this stage to construct a cDNA library. The cDNA having the sequence SEQ ID NO 1 was isolated from this cDNA library.

All the aforementioned carotene hydroxylase genes can be prepared in a manner known per se by chemical synthesis from the nucleotide building blocks such as, for example, by fragment condensation of individual overlapping, complementary nucleic acid building blocks of the double helix. Chemical synthesis of oligonucleotides is possible, for example, in a known manner by the phosphoramidite method (Voet, Voet, 2nd edition, Wiley Press New York, pages 896–897). Addition of synthetic oligonucleotides and filling in gaps using the Klenow fragment of DNA polymerase and ligation reactions, and general cloning methods, are described in Sambrook et al. (1989), Molecular cloning: A laboratory manual, Cold Spring Harbor Laboratory Press. The invention further relates to nucleic acid constructs comprising one of the carotene hydroxylase genes according to the invention described above, which are linked to one or more regulatory signals to increased gene expression.

These regulatory sequences are, for example, sequences to which inducers or repressors bind and thus regulate the expression of the nucleic acid. In addition to these new regulatory sequences or in place of these sequences it is possible for the natural regulation of these sequences still to be present in front of the actual structural genes and, where appropriate, have been genetically modified so that the natural regulation has been switched off and expression of the genes has been increased.

However, the nucleic acid construct may also have a simpler structure, that is to say no additional regulatory signals are inserted in front of the aforementioned carotene hydroxylase genes, and the natural promoter with its regulation is not deleted. Instead, the natural regulatory sequence is mutated so that regulation no longer takes place, and gene expression is increased. These modified promoters may also be placed alone in front of the natural genes to increase the activity. The nucleic acid construct may additionally advantageously contain one or more so-called enhancer sequences functionally linked to the promoter, which make increased expression of the nucleic acid sequence possible. It is also possible to insert additional advantageous sequences at the 3' end of the DNA sequences, such as further regulatory elements or terminators. The aforementioned carotene hydroxylase genes may be present in one or more copies in the gene construct.

Advantageous regulatory sequences for the nucleic acid constructs according to the invention, for the process described below for preparing xanthophylls and for the genetically modified organisms described below are present, for example, in promoters such as cos, tac, trp, tet, trp-tet, lpp, lac, lpp-lac, $lacI^q$, T7, T5, T3, gal, trc, ara, SP6, $\lambda$-$P_R$ or in the $\lambda$-$P_L$ promoter, which are advantageously used in Gram-negative bacteria.

Further advantageous regulatory sequences are present, for example, in the Gram-positive promoters amy and SPO2, in the yeast or fungal promoters ADC1, MF$\alpha$, AC, P-60, CYCI, GAPDH, TEF, rp28, ADH or in the plant promoters CaMV/35S [Franck et al., Cell 21(1980) 285–294], PRP1 [Ward et al., Plant.Mol. Biol.22(1993)], SSU, OCS, leb4, usp, STLS1, B33, nos or in the ubiquitin or phaseolin promoter.

Particularly advantageous are those plant promoters which ensure specific expression in tissues or plant parts in which the biosynthesis of carotenoids or precursors thereof takes place or in which the products advantageously accumulate.

Particular mention should be made of promoters for the whole plant on the basis of constitutive expression, such as, for example, the CaMV promoter, the OCS promoter from *Agrobacterium* (octopine synthase), the NOS promoter from *Agrobacterium* (nopaline synthase), the ubiquitin promoter, promoters of vacuolar ATPase subunits or the promoter of a proline-rich protein from wheat (WO 9113991), seed-specific promoters such as, for example, the phaseolin promoter and the USP promoter from *Vicia faba*, the promoter of the legumin gene from *Vicia* (leb4) or the Bce4 gene promoter from *Brassica* (WO 9113980), specific promoters for green tissues such as, for example, the SSU promoter (small subunit) of rubisco (ribulose-1,5-bisphosphate carboxylase) or the STLS1 promoter (*Solanum tuberosum*, light harvesting system 1 from potato), mesophyll-specific promoters such as, for example, the FBPase promoter of the cytosolic FBPase from potato (WO9705900), specific promoters for tubers, storage roots or roots, such as, for example, the patatin promoter class I (B33), the promoter of the cathepsin D inhibitor from potato, the promoter of starch synthase (GBSS1) or the sporamin promoter, fruit-specific promoters such as, for example, the fruit-specific promoter from tomato (EP409625), fruit ripening-specific promoters such as, for example, the fruit ripening-specific promoter from tomato (WO 9421794), flower-specific promoters such as, for example, the phytoene synthase promoter (WO9216635) or the promoter of the P-rr gene (WO9822593), specific plastid or chromoplast promoters such as, for example, the RNA polymerase promoter (WO9706250) or pathogen- or chemically inducible promoters such as, for example, the PRP1 promoter, a benzenesulfonamide-inducible (EP 388186), a tetracycline-inducible (Gatz et al., (1992) Plant J. 2,397–404), an abscisic acid-inducible (EP335528) or an ethanol- or cyclohexanone-inducible (WO9321334) promoter.

It is also possible and advantageous to use the promoter of phosphoribosyl-pyrophosphate amidotransferase from *Glycine max* (see also Genbank accession number U87999) or another node-specific promoter as in EP 249676.

It is possible in principle to use all natural promoters with their regulatory sequences like those mentioned above for the process according to the invention. It is additionally possible and advantageous to use synthetic promoters.

The nucleic acid construct may also contain other genes which are to be introduced into the organisms. These genes may be under separate regulation or under the same regulatory region as the above-described carotene hydroxylase genes. Examples of these genes are other biosynthetic genes of carotenoid biosynthesis which make increased synthesis possible. Particular mention may be made of other genes of carotenoid biosynthesis which are biochemically limiting, such as the genes encoding phytoene synthase, phytoene desaturase, isopentyl-pyrophosphate isomerase or β-cyclase.

Genes encoding an isopentyl-pyrophosphate isomerase are known, for example, from the organisms Phaffia rhodozyma and *Haematococcus pluvialis* (EP 769 551) or *Arabidopsis thaliana* and *Tagetes* (Marigold) (WO 9736998).

Genes encoding a phytoene synthase are known, for example, from the organisms *Erwinia uredovora* (EP 393690), *Erwinia herbicola* (WO 9113078), tomato (WO 9109128), melon (WO 9602650), *Flavobacterium* (EP 747483) or *Nicotiana* (U.S. Pat. No. 5,705,624).

Genes encoding a phytoene desaturase are known, for example, from the organisms *Erwinia uredovora* (EP 393690), *Erwinia herbicola* (WO 9113078), *Nicotiana* (U.S. Pat. No. 5,539,093) or *Flavobacterium* (EP 747483).

Genes encoding a β-cyclase are known, for example, from the organisms *Erwinia uredovora* (EP 393690), *Erwinia herbicola* (WO 9113078), *Flavobacterium* (EP 747483), tobacco and tomato (WO 9628014) or *Capsicum annuum* (WO 9636717).

The invention further relates to a process for preparing the genetically modified organisms described below, wherein the carotene hydroxylase genes according to the invention or the nucleic acid constructs according to the invention are introduced into the genome of the initial organism. By initial organisms are meant the organisms before the genetic modification according to the invention.

The carotene hydroxylase genes according to the invention or the nucleic acid constructs according to the invention can in principle be introduced by all methods known to the skilled worker into the initial organisms described below, which are genetically modified thereby.

They are advantageously introduced into the initial organisms or cells thereof by transformation, transfection, electroporation, using the so-called particle gun or by microinjection.

The skilled worker can find appropriate methods for microorganisms in the textbooks by Sambrook, J. et al. (1989) Molecular cloning: A laboratory manual, Cold Spring Harbor Laboratory Press, by F. M. Ausubel et al. (1994) Current protocols in molecular biology, John Wiley and Sons, by D. M. Glover et al., DNA Cloning Vol. 1, (1995), IRL Press (ISBN 019-963476-9), by Kaiser et al. (1994) Methods in Yeast Genetics, Cold Spring Harbor Laboratory Press or Guthrie et al. Guide to Yeast Genetics and Molecular Biology, Methods in Enzymology, 1994, Academic Press.

Examples of advantageous methods which may be mentioned are those such as the introduction of the DNA by homologous or heterologous recombination, for example using the ura-3 gene, specifically the ura-3 gene from Ashbya, as described in the German Application DE 19801120.2, and/or by the REMI method (="restriction enzyme mediated integration) which is described below.

The REMI technique is based on the cotransformation of a linear DNA construct which has been cut at both ends with the same restriction endonuclease, together with the restriction endonuclease which was used for this restriction of the DNA construct, into an organism. The restriction endonuclease then cuts the genomic DNA of the organism into which the DNA construct has been introduced together with the restriction enzyme. This leads to an activation of the cell's own repair mechanisms. These repair mechanisms repair the strand breaks in the genomic DNA which have been caused by endonuclease, and during this also incorporate with a certain frequency the cotransformed DNA construct into the genome. Ordinarily, the restriction cleavage sites are retained at both ends of the DNA during this.

This technique was described by Bölker et al. (Mol Gen Genet, 248, 1995: 547–552) for the insertion mutagenesis of fungi. The method was used by Von Schiestl and Petes (Proc. Natl. Acad. Sci. USA, 88, 1991: 7585–7589) to find out whether there is heterologous recombination in *Saccharomyces*. The method has been described by Brown et al. (Mol. Gen. Genet. 251, 1996: 75–80) for the stable transformation and regulated expression of an inducible reporter gene.

It is possible using the REMI method to position the nucleic acid fragments according to the invention or the aforementioned carotene hydroxylase genes according to the invention at transcriptionally active sites in the genome.

It is possible and advantageous to clone the nucleic acids together with at least one reporter gene into a DNA construct, which is introduced into the genome. This reporter gene ought to make detectability easy by a growth, fluorescence, chemo- or bioluminesence assay or by a photometric measurement. Examples which may be mentioned of reporter genes are antibiotic resistance genes, hydrolase genes, fluorescent protein genes, bioluminescence genes, glucosidase genes, the luciferase gene, β-galactosidase gene, gfp gene, lipase gene, esterase gene, peroxidase gene, β-lactamase gene, acetyl-, phospho- or adenyltransferase gene. These genes make it possible easily to measure and quantify the transcription activity and thus the expression of the genes. This means that it is possible to identify sites in the genome which have a productivity differing by up to a factor of 2.

If it is intended to introduce a plurality of genes, such as, for example, further crt genes of carotenoid biosynthesis, into the organism, they can all be introduced together with a reporter gene in a single vector, or each individual gene with a reporter gene can be introduced in one vector in each case, into the organism, it being possible to introduce the various vectors at the same time or successively. It is also possible to insert gene fragments coding for the respective activities in the REMI techniques.

Restriction enzymes suitable in principle for integrating the carotene hydroxylase genes or nucleic acid constructs according to the invention into the genome of initial organisms are all known ones. Restriction enzymes which recognize only 4 base pairs as restriction cleavage site are less preferred because they cut too often in the genome or in the vector to be integrated, and preferred enzymes recognize 6, 7, 8 or more base pairs as cleavage site, such as BamHI, EcoRI, BglII, SphI, SpeI, XbaI, XhoI, NcoI, SalI, ClaI, KpnI, HindIII, SacI, PstI, BpnI, NotI, SrfI or SfiI, to mention only a few of the possible enzymes. It is advantageous if the enzymes used no longer have cleavage sites in the DNA to be introduced; this increases the efficiency of integration. Ordinarily, 5 to 500 U, preferably 10 to 250, particularly preferably 10 to 100 U of the enzymes are used in the REMI mixture. The enzymes are advantageously employed in an aqueous solution which contains substances for osmotic stabilization, such as sugars such as sucrose, trehalose or glucose, polyols such as glycerol or polyethylene glycol, a buffer with an advantageous buffering in the range of pH 5 to 9, preferably 6 to 8, particularly preferably 7 to 8, such as tris, MOPS, HEPES, MES or PIPES and/or substances to stabilize the nucleic acids, such as inorganic or organic salts of Mg, Cu, Co, Fe, Mn or Mo. It is also possible where appropriate for the substances to be present, such as EDTA, EDDA, DTT, β-mercaptoethanol or nuclease inhibitors. However, it is also possible to carry out the REMI technique without these additions.

The process is carried out at a temperature in the range from 5 to 80° C., preferably from 10 to 60° C., particularly preferably from 20 to 40° C. Other known methods for destabilizing cell membranes are suitable for the process, such as, for example, electroporation, fusion with loaded vesicles or destabilization with various alkali metal or alkaline earth metal salts such as lithium, rubidium or calcium salts, with lithium salts being preferred.

The nucleic acids can be used for the reaction according to the invention directly after isolation or after purification.

The introduction of the carotene hydroxylase genes according to the invention or the nucleic acid constructs according to the invention into plants can in principle take place by all methods known to the skilled worker.

The transfer of foreign genes into the genome of a plant is referred to as transformation. In this case, the described methods for the transformation and regeneration of plants from plant tissues or plant cells for transient or stable transformation are utilized.

Suitable methods are protoplast transformation by polyethylene glycol-induced DNA uptake, the use of a gene gun, electroporation, incubation of dry embryos in DNA-containing solution, microinjection and *Agrobacterium*-mediated gene transfer. The methods mentioned are described, for example, in B. Jenes et al., Techniques for Gene Transfer, in: Transgenic Plants, Vol. 1, Engineering and Utilization, edited by S. D. Kung and R. Wu, Academic Press (1993) 128–143, and in Potrykus Annu. Rev. Plant Physiol. Plant Molec. Biol. 42 (1991) 205–225.

The construct to be expressed is preferably cloned into a vector which is suitable for transforming *Agrobacterium tumefaciens*, for example pBin19 (Bevan et al., Nucl. Acids Res. 12 (1984) 8711).

Transformation with *Agrobacterium tumefaciens* is described, for example, by Höfgen and Willmitzer in Nucl. Acids Res. (1988) 16, 9877.

*Agrobacteria* transformed with an expression vector according to the invention can likewise be used in a known manner for transforming plants, in particular tagetes, sunflower, *arabidopsis*, tobacco, red pepper, soybean, tomato, aubergine, paprika, carrot, potato, corn, lettuce and *brassica* species, oats, rye, wheat, triticale, millet, rice, alfalfa, flax, brassicaceae such as, for example, oilseed rape or canola, sugar beet, sugar cane or wood plants such as, for example, aspen or yew, for example by bathing wounded leaves or pieces of leaves in a solution of *agrobacteria* and then cultivating in suitable media.

The genetically modified plant cells can be regenerated by all methods known to the skilled worker. Appropriate methods can be found in the abovementioned publications by S. D. Kung and R. Wu, Potrykus or Höfgen and Willmitzer.

There is a large number of possibilities for increasing the enzymic activity of the carotene hydroxylase gene products in the cell.

One possibility is to modify the endogenous carotene hydroxylase genes so that they code for enzymes having a carotene hydroxylase activity which is higher than the initial enzymes. Another increase in the enzymic activity can be achieved, for example, by modifying the catalytic sites to increase substrate conversion or by aborting the effect of enzyme inhibitors, that is to say they have an increased specific activity or their activity is not inhibited. The enzymic activity can also be increased in a further advantageous embodiment by increasing enzyme synthesis in the cell, for example by eliminating factors which repress enzyme synthesis or by increasing the activity of factors or regulatory elements which promote enhanced synthesis, or preferably by introducing further gene copies. This measure increases the total activity of the gene products in the cell without altering the specific activity. It is also possible to use a combination of these methods, that is to say increasing the specific activity plus increasing the total activity. These modifications can in principle be introduced by all methods known to the skilled worker into the nucleic acid sequences of the genes, regulatory elements or promoters thereof. It is possible for this purpose to subject the sequences, for example, to a mutagenesis such as a site directed mutagenesis as described in D. M. Glover et al., DNA Cloning Vol. 1, (1995), IRL Press (ISBN 019-963476-9), chapter 6, page 193 et seq.

Spee et al. (Nucleic Acids Research, Vol. 21, No. 3, 1993: 777–778) describes a PCR method using dITP for random mutagenesis The use of an in vitro recombination technique for molecular evolution is described by Stemmer (Proc. Natl. Acad. Sci. USA, Vol. 91, 1994: 10747–10751).

Moore et al. (Nature Biotechnology Vol. 14, 1996: 458–467) describe combination of the PCR and recombination methods.

The modified nucleic acid sequences are subsequently returned to the organisms via vectors.

For increasing enzymic activities it is also possible to place modified promoter regions in front of the natural genes so that expression of the genes is increased and thus the activity is eventually raised. Sequences can also be introduced at the 3' end, for example to increase the stability of the mRNA and thus make increased translation possible. This likewise leads to higher enzymic activity.

In a further preferred embodiment, the carotene hydroxylase genes or nucleic acid constructs according to the invention are, for expression in one of the organisms described below, inserted into a vector such as, for example, a plasmid, a phage or other DNA which makes optimal expression of the genes possible in the prokaryotic or eukaryotic organisms. This vector may contain the ATG start codon for expression of the protein according to the invention.

Examples of suitable plasmids in *E. coli* are pLG338, pACYC184, pBR322, pUC18, pUC19, pKC30, pRep4, pHS1, pHS2, pPLc236, pMBL24, pLG200, pUR290, pIN-III[113]-B1, λgt11, pBdCI, the pET vector series (Novagen and Stratagene), PMAL or the pQE vector series (Qiagen), in fungi pALS1, pIL2 or pBB116, in yeasts 2μ, pAG-1, YEp6, YEp13 or pEMBLYe23 or in plants pLGV23, pGHlac⁺, pBIN19, pAK2004, pDH51, or derivatives of the aforementioned plasmids.

Said plasmids represent a small selection of the possible plasmids. Further plasmids are well known to the skilled worker and can be found, for example, in the book Cloning Vectors (Eds. Pouwels P. H. et al. Elsevier, Amsterdam-New York-Oxford, 1985, ISBN 0 444 904018). Suitable plant vectors are described inter alia in "Methods in Plant Molecular Biology and Biotechnology" (CRC Press), chapters 6/7, pp. 71–119.

It is advantageous for expression of the other genes present if the nucleic acid fragment also contains in addition 3' and/or 5' terminal regulatory sequences to increase expression, which are selected for optimal expression depending on the selected host organism and gene or genes.

These regulatory sequences are intended to make specific expression of the genes and protein expression possible.

This may mean, for example, depending on the host organism that the gene is expressed and/or overexpressed only after induction, or that it is immediately expressed and/or overexpressed.

The regulatory sequences or factors may moreover preferably have a beneficial effect on expression of the introduced genes, and thus increase it. Enhancement of the regulatory elements is thus advantageously possible at the level of transcription by using strong transcription signals such as promoters and/or enhancers. However, it is also possible to enhance translation by, for example, improving the stability of the mRNA.

In a further embodiment of the vector, the nucleic acid construct according to the invention may also advantageously be introduced in the form of a linear DNA into the host organisms and be integrated into the genome of the host organism by heterologous or homologous recombination. This linear DNA may consist of a linearized plasmid or only of the nucleic acid fragment as vector.

It is also possible to use as vector any plasmid which undergoes autonomous replication in the cell, but also, as described above, a linear DNA fragment which integrates into the genome of the host. This integration can take place by heterologous or homologous recombination, but preferably, as mentioned, by homologous recombination (Steiner et al., Genetics, Vol. 140, 1995: 973–987). It is moreover possible for the aforementioned carotene hydroxylase genes to be present singly in the genome at various sites or on various vectors or to be present together in the genome or on one vector.

The invention further relates to the use of the carotene hydroxylase genes according to the invention for producing genetically modified organisms.

The invention further relates to a correspondingly genetically modified organism, with the expression of the carotene hydroxylase genes according to the invention being increased by comparison with a wild type in the case where the initial organism contains a carotene hydroxylase gene according to the invention, or being caused in the case where the initial organism does not contain a carotene hydroxylase gene according to the invention, by the genetic modification.

A genetically modified organism means an organism in which the carotene hydroxylase genes or nucleic acid constructs according to the invention have been inserted, preferably by one of the methods described above.

The genetically modified organism contains at least one carotene hydroxylase gene according to the invention or at least one nucleic acid construct according to the invention. Depending on the initial organism, the nucleic acid may be present inside or outside the chromosome.

Carotenoid metabolism in the genetically modified organisms is preferably altered by comparison with the wild type.

Suitable genetically modified organisms are in principle all organisms able to synthesize xanthophylls.

Preferred initial organisms are those naturally able to synthesize xanthophylls. However, initial organisms able to synthesize xanthophylls because of the introduction of carotenoid biosynthesis genes are also suitable.

Initial organisms mean prokaryotic or eukaryotic organisms such as, for example, microorganisms or plants. Preferred microorganisms are bacteria, yeasts, algae or fungi.

Bacteria which can be used are both bacteria which are able, because of the introduction of carotenoid biosynthesis genes of a carotenoid-producing organism to synthesize xanthophylls, such as, for example, bacteria of the genus *Escherichia*, which contain, for example, crt genes from *Erwinia*, and bacteria which are intrinsically able to synthesize xanthophylls, such as, for example, bacteria of the genus *Erwinia, Agrobacterium, Flavobacterium, Alcaligenes* or Cyanobacteria of the genus *Synechocystis*. Preferred bacteria are *Escherichia coli, Erwinia herbicola, Erwinia uredovora, Agrobacterium aurantiacum, Alcaligenes* sp. PC-1, *Flavobacterium* sp. strain R1534 or the Cyanobacterium *Synechocystis* sp. PCC6803.

Preferred uses are *Candida, Saccharomyces, Hansenula* or *Pichia*.

Preferred fungi are *Aspergillus, Trichoderma, Ashbya, Neurospora, Fusarium* or other fungi described in Indian Chem Engr. Section B. Vol 37, No. 1,2 (1995) on page 15, Table 6.

Preferred algae are green algae such as, for example, algae of the genus Haematococcus, Phaedactylum tricornatum, Volvox or Dunaliella. Particular preferred algae are Haematococcus luvialis or Dunaliella bardawil.

In a preferred embodiment, plants are used as initial organisms and, accordingly, also as genetically modified organisms. Examples of preferred plants are tagetes, sunflower, *arabidopsis*, tobacco, red pepper, soybean, tomato, aubergine, paprika, carrot, potato, corn, lettuce and *brassica* species, oats, rye, wheat, triticale, millet, rice, alfalfa, flax, brassicaceae such as, for example, oilseed rape or canola, sugar beet, sugar cane or woody plants such as, for example aspen or yew.

Particular preference is given to *Arabidopsis thaliana*, Tagetes erecta, oilseed rape, canola, potatoes, and oilseeds and typical carotenoid producers such as soybean, sunflower, paprika, carrot, pepper or corn.

The invention further relates to a process for the preparation of xanthophyll derivatives, which comprises converting a β-ionone structural element into a 3-hydroxy-β-ionone structural element and/or a 4-keto-β-ionone structural element into a 3-hydroxy-4-keto-β-ionone structural element in the presence of the protein according to the invention.

Xanthophyll derivatives mean xanthophylls, preferably xanthophylls containing at least one hydroxyl group, such as, for example, zeaxanthin, β-cryptoxanthin, 3'-hydroxyechinenone, 3-hydroxyechinenone, adonixanthin (4-ketozeaxanthin), astaxanthin, phoenicoxanthin (adonirubin), α-cryptoxanthin or lutein or derivatives thereof having up to 40 C atoms and containing at least one 3-hydroxy-β-ionone or at least one 3-hydroxy-4-keto-β-ionone structural element in the molecule, such as, for example, 3-hydroxy-6-vinyl-β-ionone, 3-hydroxy-4-keto-6-vinyl-β-ionone, 3-hydroxyretinol, 3-hydroxy-4-ketoretinol, 3-hydroxyretinal, 3-hydroxy-4-ketoretinal, 3-hydroxyretinoic acid or 3-hydroxy-4-ketoretinoic acid.

Preferred xanthophyll derivatives are zeaxanthin, lutein and astaxanthin.

In the process according to the invention there is conversion in the presence of the proteins according to the invention of a β-ionone structural element into a 3-hydroxy-β-ionone structural element, such as β-carotene into zeaxanthin, β-carotene into β-cryptoxanthin, β-cryptoxanthin into zeaxanthin, echinenon into 3'-hydroxyechinenone, 3-hydroxyechinenone into adonixanthin (4-ketozeaxanthin), α-carotene into α-cryptoxanthin or a chemical compound having up to 40 C atoms and containing a β-ionone ring into the corresponding 3-hydroxy-β-ionone compound or a 4-keto-β-ionone structural element into a 3-hydroxy-4-keto-β-ionone structural element, such as canthaxanthin into astaxanthin, canthaxanthin in phoenicoxanthin (adonirubin), phoenicoxanthin (adonirubin) into astaxanthin, echinenone into 3-hydroxyechinenone, 3'-hydroxyechinenone into adonixanthin (4-ketozeaxanthin) or a chemical compound having up to 40 C atoms and containing a 4-keto-β-ionone ring into the corresponding 3-hydroxy-4-keto-β-ionone compound.

In a preferred embodiment of the process, an aforementioned genetically modified organism according to the invention is cultivated, the latter organism is harvested, and subsequently the xanthophyll derivatives are isolated from the organism.

Cultivation of the genetically modified organism according to the invention takes place in a manner known per se, such as cultivation of the appropriate wild type, for example in the case of microorganisms in a suitable medium such as, for example, on agar plates or in suspension culture, or in the case of plants in soil or appropriately suitable nutrient media. By harvesting is meant in the case of microorganisms the isolation of the microorganisms, and in the case of plants the cutting off of the plant or, where appropriate, particular plant parts containing the xanthophyll derivatives. The xanthophyll derivatives are isolated in a manner known per se, for example by disruption of the organism cells, extraction of the xanthophyll derivatives and subsequent purification of the xanthophyll derivatives by chemical or physical separation methods such as extraction or chromatography.

The invention further relates to the use of the carotene hydroxylase according to the invention or of the carotene hydroxylase genes according to the invention for preparing xanthophyll derivatives.

The following examples illustrate the invention

EXAMPLE 1

Incorporation of the Carotene Hydroxylase Gene into a β-Carotene Producing e. Coli, Fermentation of the Transgenic Organism and Isolation of the Xanthophylls General Methods Isolation of the Carotenoids To isolate the carotenoids (carotenes and xanthophylls), the E. coli cells were collected by centrifugation, and the resulting cell material was freeze dried for 24 h. The freeze-dried cells were resuspended in acetone and extracted twice with acetone at 55° C. for 15 min. The combined extracts were washed with a diethyl ether/petroleum ether (boiling point 35–80° C.) mixture (1:9, v/v) in a separating funnel and concentrated to dryness under nitrogen in a rotary evaporator.

HPLC Analysis

The extracts were fractionated using a Nucleosil 100-5 C18 column (Macherey-Nagel) with an eluent flow rate of 1.5 ml/min. The eluent used to fractionate the β-carotene and the hydroxylated xanthophylls in Example 1 was an acetonitrile/methanol/2-propanol mixture (85:10:5, v/v/v; flow).

To fractionate the xanthophylls with keto groups in Example 2, an acetonitrile/methanol/$H_2O$ mixture (50:44:6, v/v/v) was used as eluent 1 for 22 min, and methanol was used as eluent 2. Detection took place directly using the Waters 994 diode array detector. A comparison standard for the HPLC analysis were β-carotene, astaxanthin and zeaxanthin purchased from Sigma or Roth.

1.1 Production of β-Carotene-Producing E. coli

The organism used comprised E. coli cells of the strain JM101. The plasmid pACCAR16DcrtX contains the bacterial carotenoid biosynthesis genes crtE, crtB, crtI and crtY from Erwinia uredovora and results in the biosynthesis of β-carotene (N. Misawa et al., J. Bacteriol. 172 (1990) 6704–6712; Biochem. Biophys. Res. Commun. 209 (1995) 867–876)

To prepare this plasmid, a 6.0 kb Asp718(KpnI)-EcoRI fragment of the carotenoid biosynthesis gene cluster from Erwinia uredovora (Plasmid pCAR16delB) was cloned into the EcoRI site of the plasmid pACY184 (R. E. Rose, Nucl. Acids Res. 16 (1988) 355). The plasmid pCAR16delB contains a frameshift mutation in the β-carotene hydroxylase ORF (open reading frame) (Misawa et al., Biochem. Biophys. Res. Commun. 209 (1995) 867–876). It is therefore impossible for the resulting β-carotene to be hydroxylated to zeaxanthin.

Insertion of the plasmid pACCAR16DcrtX into E. coli and preparation and isolation of transformed E. coli cells took place in a manner known per se, as described in Sambrook et al., Molecular cloning: a laboratory manual, 2nd edn. Cold Spring Harbor Laboratory Press, Cold Spring Harbor, N.Y., 1989.

1.2 Construction of a Haematococcus pluvialis λcDNA Expression Library and Isolation of the Plasmid Containing the Carotene Hydroxylase Gene Haematococcus pluvialis Flotow NIES-144 originated from the National Institute for Environmental Studies (NIES), Tsukuba, Japan. The basal medium (pH 6.8) in the growth phase of Haematococcus pluvialis contained per liter 1.2 g of sodium acetate, 2.0 g of yeast extract, 0.4 g of L-asparagine, 0.2 g of $MgCl_{2*6}H_2O$, 0.01 g of $FeSO_4.7H_2O$, and 0.02 g of $CaCl_{2*2}H_2O$. Haematococcus pluvialis was grown at 20° C. with a dark/light cycle of 12 h light (20 $\mu E/m^2 s$) and 12 h dark for 4 days. To induce astaxanthin biosynthesis and cyst cell formation, after 4 days sodium acetate and $FeSO_4$ were added to a concentration of 45 mM and 450 μM respectively. After the addition, the light conditions were changed to continuous light (125 $\mu E/m^2 s$) as described in Kajiwara et al., Plant Mol. Biol. 29 (1995) 343–352. After induction of cyst cell formation for 8 h, the RNAs of Haematococcus pluvialis were isolated to construct a cDNA library from the cyst cells.

The poly(A)RNA was purified using oligo(dT)-cellulose (Biolabs). Synthesis of the cDNAs and construction of the λZAP expression library took place with the aid of the cDNA Synthesis and ZAP-cDNA Gigapack III Gold Cloning Kit (Stratagene). The first strand of the cDNA was synthesized using MMLV reverse transcriptase and a poly (dT) primer containing an XhoI restriction enzyme recognition site in accordance with the Stratagene instructions for use. The second strand was synthesized correspondingly using DNA polymerase I. Blunt DNA ends were produced by filling in with Pfu DNA polymerase, and EcoRI adapters were ligated thereto. The resulting cDNA fragments were then fractionated according to size and subsequently ligated into the EcoRI-XhoI recognition site of the Uni-ZAP XR vector. After isolation and purification of the positive carotene hydroxylase plaque, the pBluescript phagemid containing the carotene hydroxylase cDNA was recovered by in vivo cutting out by use of the ExAssist helper phage and the SOLR E. coli strain, in accordance with the Stratagene instructions for use. The resulting plasmid contains in addition to the short adapter sequences at the 5'-(5'-AATTCG-GCACGAG-3') and 3' (5'-TCGAG-3') ends according to DNA sequence analysis a 1608 bp-long cDNA fragment ligated into the EcoRI and XhoI restriction site of the multiple cloning site. This plasmid was used for insertion of the carotene hydroxylase gene into the β-carotene-producing E. coli cells as described under 1.1.

1.3. Incorporation of the Carotene Hydroxylase Gene into β-Carotene-Producing E. coli Cells, Cultivation of the Transformed Cells and Isolation of the Xanthophylls Zeaxanthin and β-Cryptoxanthin Transformation of the β-carotene-producing *E. coli* cells containing the plasmid pACCAR16DcrtX, described under 1.1., with the plasmid containing the carotene hydroxylase gene, described under 1.3., took place in a manner known per se as described in J. Sambrook et al., Molecular cloning: a laboratory manual, 2nd edn. Cold Spring Harbor Laboratory Press, Cold Spring Harbor, N.Y., 1989.

The transformed *E. coli* cells were cultured in LB medium at 28° C. with addition of ampicillin (50 µg/ml; for the plasmid containing the carotene hydroxylase gene) and chloramphenicol (30 µg/ml; plasmid pACCAR16DcrtX) for 48 h.

The carotenoids were isolated as described under the general methods. FIG. 1 shows the HPLC diagram for the carotenoids extracted from (A) *E. coli* cells containing the plasmid pACCAR16DcrtX from 1.1 and (B) *E. coli* cells containing the plasmid pACCAR16DcrtX together with the carotene hydroxylase gene from 1.2.

The peak numbers in FIG. 1 mean

| | |
|---|---|
| 3 | zeaxanthin |
| 5 | β-cryptoxanthin |
| 6 | β-carotene |

As is evident from FIG. 1, the transformed *E. coli* cells produce, due to incorporation of the carotene hydroxylase gene according to the invention, the hydroxylated xanthophylls zeaxanthin and β-cryptoxanthin, whereas only β-carotene is produced without the transformation. The carotene hydroxylase according to the invention is accordingly able to convert β-carotene into β-cryptoxanthin, β-cryptoxanthin into zeaxanthin or β-carotene into zeaxanthin.

EXAMPLE 2

Incorporation of the carotene hydroxylase gene and the β-carotene ketolase gene (bkt) from *Haematococcus pluvialis* into β-carotene-producing *E. coli* cells, cultivation of the transformed cells and isolation of the xanthophylls astaxanthin, canthaxanthin, adonixanthin, zeaxanthin and β-cryptoxanthin

2.1 Preparation of a Plasmid Containing the β-Carotene Ketolase Gene (bkt) from Haematococcus pluvialis To prepare the plasmid pRKbkt1 (Kajiwara et al., Plant Mol. Biol. 29 (1995) 343–352) containing the β-carotene ketolase gene from *Haematococcus pluvialis*, a 1 kb product of a PvuII partial digest of the pUC19bkt plasmid was fractionated by agarose gel electrophoresis (Breitenbach et al., FEMS Microbiol. Lett. 140 (1996) 241–246). This DNA fragment contains the lacZ promoter together with the ORF (open reading frame) of the ketolase and was subcloned into the plasmid pRK404 which had previously been digested with HindIII and treated with the Klenow enzyme.

The resulting plasmid pRKbkt1 was inserted once alone and once together with the carotene hydroxylase gene plasmid described under 1.2 into the β-carotene-producing *E. coli* cells.

2.2 Incorporation of the Plasmid pRKbkt1 into β-Carotene-Producing E. coli Cells, Cultivation of the Transformed Cells and Isolation of the Xanthophyll Canthaxanthin Transformation of the β-carotene-producing *E. coli* cells containing the plasmid pACCAR16DcrtX, described under 1.1., with the plasmid pRKbkt1 containing the β-carotene ketolase gene (bkt), described under 2.1., took place in a manner known per se as described in J. Sambrook et al., Molecular cloning: a laboratory manual, 2nd edn. Cold Spring Harbor Laboratory Press, Cold Spring Harbor, N.Y., 1989.

The transformed *E. coli* cells were cultured in analogy to the description under 1.3. in LB medium at 28° C., but with the addition of chloramphenicol (30 µg/ml; plasmid pACCAR16DcrtX), tetracycline (10 µg/ml; plasmid pRKbkt1) and isopropyl β-D-thio-galactopyranoside (0.5 mM) for 48 h.

The carotenoids were isolated as described under the general methods.

Figure 2:
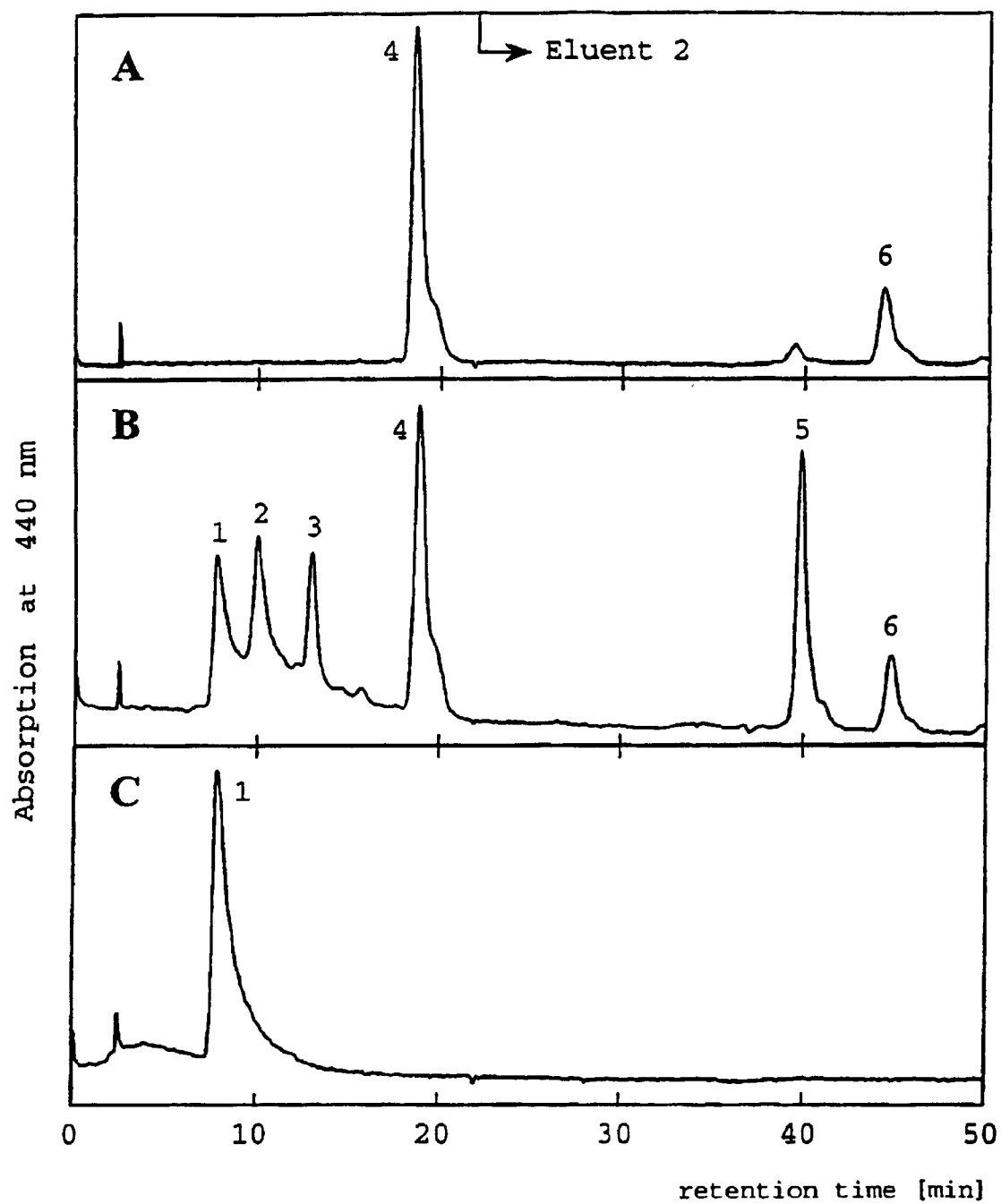
FIG. 2 shows the HPLC diagrams for the carotenoids extracted from (A) *E. coli* cells containing the plasmid pACCAR16DcrtX with the plasmid pRKbkt1, (B) *E. coli* cells containing the plasmid pACCAR16DcrtX together with the plasmid pRKbkt1 and the carotene hydroxylase gene, (C) shows astaxanthin as comparison standard.

FIG. 2 (A) shows HPLC-diagram of the carotenoids extracted from *E. coli* cells containing the plasmid pACCAR16DcrtX together with the plasmid pRKbkt1, containing the β-carotene ketolase gene (bkt). Incorporation of the plasmid pRKbkt1 results in the transformed *E. coli* cells producing the xanthophyll with a keto group canthaxanthin.

2.3 Incorporation of the Plasmid pRKbkt1 and the Carotene Hydroxylase Gene into β-carotene-Producing E. coli Cells, Cultivation of the Transformed Cells and Isolation of the Xanthophylls, Astaxanthin, Canthaxanthin, Adonixanthin, Zeaxanthin and β-Cryptoxanthin Transformation of the β-carotene-producing *E. coli* cells containing the plasmid pACCAR16DcrtX, described under 1.1., with the plasmid pRKbkt1 containing the β-carotene ketolase gene (bkt), described under 2.1., with the plasmid containing the carotene hydroxylase gene, described under 1.3, took place in a manner known per se as described in J. Sambrook et al., Molecular cloning: a laboratory manual, 2nd edn. Cold Spring Harbor Laboratory Press, Cold Spring Harbor, N.Y., 1989.

The transformed *E. coli* cells were cultured in analogy to the description under 1.3. in LB medium at 28° C., but with the addition of ampicillin (50 µg/ml; plasmid containing the carotene hydroxylase gene), chloramphenicol (30 µg/ml; plasmid pACCAR16DcrtX), tetracycline (10 µg/ml; plasmid pRKbkt1) and isopropyl β-D-thio-galactopyranoside (0.5 mM) for 48 h.

The carotenoids were isolated as described under the general methods. FIG. 2 shows the HPLC diagrams for the carotenoids extracted from (A) *E. coli* cells containing the plasmid pACCAR16DcrtX from 1.1. together with the plasmid pRKbkt1 and (B) *E. coli* cells containing the plasmid pACCAR16DcrtX together with the plasmid pRKbkt1 and the carotene hydroxylase gene from 1.2.

FIG. 2 (C) shows astaxanthin as comparison standard.

The peak numbers in FIG. 2 mean

| | |
|---|---|
| 1 | astaxanthin |
| 2 | adonixanthin |
| 3 | zeaxanthin |
| 4 | canthaxanthin |
| 5 | β-cryptoxanthin |
| 6 | β-carotene |

As can be seen in FIG. 2, the transformed *E. coli* cells produce, due to incorporation of the carotene hydroxylase gene according to the invention together with the plasmid pRKbkt1 containing the β-carotene ketolase gene (bkt), the hydroxylated and/or keto-containing xanthophylls astaxanthin, canthaxanthin, adonixanthin, zeaxanthin and β-cryptoxanthin, whereas only canthaxanthin is produced without the carotene hydroxylase gene according to the invention.

In enzyme studies on the β-carotene ketolase from Haematococcus pluvialis it was shown that the enzyme mainly converts β-carotene into canthaxanthin, whereas hydroxyl-containing xanthophylls such as zeaxanthin and β-cryptoxanthin are scarcely converted, and only to adonixanthin and not to astaxanthin (T. Lotan, J. Hirschberg, FEBS Lett. 364 (1995) 125–128; J. Breitenbach, N. Misawa, S. Kajiwara, G. Sandmann, FEMS Microbiol. Lett. 140 (1996) 241–246; P. D. Fraser, H. Shimada, N. Misawa, Eur. J. Biochem. 252 (1998) 229–236).

The fact that the *E. coli* cells transformed in Example 2.3 are able to produce astaxanthin proves that the carotene hydroxylase according to the invention is able to convert canthaxanthin via phoenicoxanthin (adonirubin) into astaxanthin.

The carotene hydroxylase according to the invention is accordingly able to catalyze the conversion of a β-ionone structural element into a 3-hydroxy-β-ionone structural element, such as the conversion of β-carotene into zeaxanthin, β-carotene into β-cryptoxanthin, β-cryptoxanthin into zeaxanthin, echinenone into 3'-hydroxyechinenone, 3-hydroxyechinenone into adonixanthin (4-ketozeaxanthin), α-carotene into α-cryptoxanthin or other chemical compounds which have up to 40 C atoms and contain a β-ionone ring into the corresponding 3-hydroxy-β-ionone compounds or the conversion of a 4-keto-β-ionone structural element into a 3-hydroxy-4-keto-β-ionone structural element, such as the conversion of canthaxanthin into astaxanthin, canthaxanthin into phoenicoxanthin (adonirubin), phoenicoxanthin (adonirubin) into astaxanthin, echinenone into 3-hydroxyechinenone, 3'-hydroxyechinenone into adonixanthin (4-ketozeaxanthin) or other chemical compounds which have up to 40 C atoms and contain a 4-keto-β-ionone ring into the corresponding 3-hydroxy-4-keto-β-ionone compounds.

We claim:

1. An isolated protein which has an enzymatic activity for converting β-carotene into zeaxanthin or canthaxanthin into astaxanthin, comprising the amino acid sequence SEQ ID NO. 2.

2. The isolated protein of claim 1, wherein the protein has an enzymatic activity for converting β-carotene into zeaxanthin and an enzymatic activity for converting canthaxanthin into astaxanthin.

3. An isolated nucleic acid encoding the protein of claim 1.

4. The isolated nucleic acid of claim 3, which consists of the sequence depicted in SEQ ID NO: 1.

5. A nucleic acid construe comprising the nucleic acid of claim 3 which is functionally linked to one or more signals to increase gene expression.

6. A transformed microorganism or plant wherein the the nucleic acid of claim 3 is expressed.

7. The transformed microorganism or plant of claim 6, whose carotenoid metabolism is different from that of a wild type.

8. The transformed microorganism or plant of claim 6, wherein said microorganism is eukaryotic.

9. A process for producing the transformed microorganism or plant of claim 6, which comprises introducing a nucleic acid consisting of the sequence depicted in SEQ ID NO: 1 or a nucleic acid construct comprising SEQ ID NO: 1 which is functionally linked to one or more regulation signals to microorganism or plant.

10. A process for the preparation of xanthophyll derivatives, which comprises converting a β-ionone into a 3-hydroxy-β-ionone and/or a 4-keto-β-ionone into a 3-hydroxy-4-keto-β-ionone in the presence of the protein of claim 1.

* * * * *

SEQUENCE LISTING

<160> NUMBER OF SEQ ID NOS: 2

<210> SEQ ID NO 1
<211> LENGTH: 1608
<212> TYPE: DNA
<213> ORGANISM: Haematococcus pluvialis
<220> FEATURE:
<221> NAME/KEY: CDS
<222> LOCATION: (3)..(968)

<400> SEQUENCE: 1

```
ct aca ttt cac aag ccc gtg agc ggt gca agc gct ctg ccc cac atc         47
   Thr Phe His Lys Pro Val Ser Gly Ala Ser Ala Leu Pro His Ile
     1               5                  10                  15 ggc cca cct cct cat ctc cat cgg tca ttt gct gct acc acg atg ctg        95
Gly Pro Pro Pro His Leu His Arg Ser Phe Ala Ala Thr Thr Met Leu
                 20                  25                  30 tcg aag ctg cag tca atc agc gtc aag gcc cgc cgc gtt gaa cta gcc       143
Ser Lys Leu Gln Ser Ile Ser Val Lys Ala Arg Arg Val Glu Leu Ala
             35                  40                  45 cgc gac atc acg cgg ccc aaa gtc tgc ctg cat gct cag cgg tgc tcg       191
Arg Asp Ile Thr Arg Pro Lys Val Cys Leu His Ala Gln Arg Cys Ser
         50                  55                  60 tta gtt cgg ctg cga gtg gca gca cca cag aca gag gag gcg ctg gga       239
Leu Val Arg Leu Arg Val Ala Ala Pro Gln Thr Glu Glu Ala Leu Gly
 65                  70                  75 acc gtg cag gct gcc ggc gcg ggc gat gag cac agc gcc gat gta gca       287
Thr Val Gln Ala Ala Gly Ala Gly Asp Glu His Ser Ala Asp Val Ala
 80                  85                  90                  95 ctc cag cag ctt gac cgg gct atc gca gag cgt cgt gcc cgg cgc aaa       335
Leu Gln Gln Leu Asp Arg Ala Ile Ala Glu Arg Arg Ala Arg Arg Lys
                100                 105                 110 cgg gag cag ctg tca tac cag gct gcc gcc att gca gca tca att ggc       383
Arg Glu Gln Leu Ser Tyr Gln Ala Ala Ala Ile Ala Ala Ser Ile Gly
            115                 120                 125 gtg tca ggc att gcc atc ttc gcc acc tac ctg aga ttt gcc atg cac       431
Val Ser Gly Ile Ala Ile Phe Ala Thr Tyr Leu Arg Phe Ala Met His
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 130 |     |     |     |     | 135 |     |     |     |     | 140 |     |     |     |      |
| atg | acc | gtg | ggc | ggc | gca | gtg | cca | tgg | ggt | gaa | gtg | gct | ggc | act | ctc | 479  |
| Met | Thr | Val | Gly | Gly | Ala | Val | Pro | Trp | Gly | Glu | Val | Ala | Gly | Thr | Leu |      |
|     | 145 |     |     |     |     | 150 |     |     |     |     | 155 |     |     |     |     |      |
| ctc | ttg | gtg | gtt | ggt | ggc | gcg | ctc | ggc | atg | gag | atg | tat | gcc | cgc | tat | 527  |
| Leu | Leu | Val | Val | Gly | Gly | Ala | Leu | Gly | Met | Glu | Met | Tyr | Ala | Arg | Tyr |      |
| 160 |     |     |     |     | 165 |     |     |     |     | 170 |     |     |     |     | 175 |      |
| gca | cac | aaa | gcc | atc | tgg | cat | gag | tcg | cct | ctg | ggc | tgg | ctg | ctg | cac | 575  |
| Ala | His | Lys | Ala | Ile | Trp | His | Glu | Ser | Pro | Leu | Gly | Trp | Leu | Leu | His |      |
|     |     |     |     | 180 |     |     |     |     | 185 |     |     |     |     | 190 |     |      |
| aag | agc | cac | cac | aca | cct | cgc | act | gga | ccc | ttt | gaa | gcc | aac | gac | ttg | 623  |
| Lys | Ser | His | His | Thr | Pro | Arg | Thr | Gly | Pro | Phe | Glu | Ala | Asn | Asp | Leu |      |
|     |     |     | 195 |     |     |     |     | 200 |     |     |     |     | 205 |     |     |      |
| ttt | gca | atc | atc | aat | gga | ctg | ccc | gcc | atg | ctc | ctg | tgt | acc | ttt | ggc | 671  |
| Phe | Ala | Ile | Ile | Asn | Gly | Leu | Pro | Ala | Met | Leu | Leu | Cys | Thr | Phe | Gly |      |
|     |     | 210 |     |     |     |     | 215 |     |     |     |     | 220 |     |     |     |      |
| ttc | tgg | ctg | ccc | aac | gtc | ctg | ggg | gcg | gcc | tgc | ttt | gga | gcg | ggg | ctg | 719  |
| Phe | Trp | Leu | Pro | Asn | Val | Leu | Gly | Ala | Ala | Cys | Phe | Gly | Ala | Gly | Leu |      |
|     | 225 |     |     |     |     | 230 |     |     |     |     | 235 |     |     |     |     |      |
| ggc | atc | acg | cta | tac | ggc | atg | gca | tat | atg | ttt | gta | cac | gat | ggc | ctg | 767  |
| Gly | Ile | Thr | Leu | Tyr | Gly | Met | Ala | Tyr | Met | Phe | Val | His | Asp | Gly | Leu |      |
| 240 |     |     |     |     | 245 |     |     |     |     | 250 |     |     |     |     | 255 |      |
| gtg | cac | agg | cgc | ttt | ccc | acc | ggg | ccc | atc | gct | ggc | ctg | ccc | tac | atg | 815  |
| Val | His | Arg | Arg | Phe | Pro | Thr | Gly | Pro | Ile | Ala | Gly | Leu | Pro | Tyr | Met |      |
|     |     |     |     | 260 |     |     |     |     | 265 |     |     |     |     | 270 |     |      |
| aag | cgc | ctg | aca | gtg | gcc | cac | cag | cta | cac | cac | agc | ggc | aag | tac | ggt | 863  |
| Lys | Arg | Leu | Thr | Val | Ala | His | Gln | Leu | His | His | Ser | Gly | Lys | Tyr | Gly |      |
|     |     |     | 275 |     |     |     |     | 280 |     |     |     |     | 285 |     |     |      |
| ggc | gcg | ccc | tgg | ggt | atg | ttc | ttg | ggt | cca | cag | gag | ctg | cag | cac | att | 911  |
| Gly | Ala | Pro | Trp | Gly | Met | Phe | Leu | Gly | Pro | Gln | Glu | Leu | Gln | His | Ile |      |
|     |     | 290 |     |     |     |     | 295 |     |     |     |     | 300 |     |     |     |      |
| cca | ggt | gcg | gcg | gag | gag | gtg | gag | cga | ctg | gtc | ctg | gaa | ctg | gac | tgg | 959  |
| Pro | Gly | Ala | Ala | Glu | Glu | Val | Glu | Arg | Leu | Val | Leu | Glu | Leu | Asp | Trp |      |
|     | 305 |     |     |     |     | 310 |     |     |     |     | 315 |     |     |     |     |      |
| tcc | aag | cgg | tagggtgcgg | | aaccaggcac | | | gctggtttca | | | cacctcatgc | | | | | 1008 |
| Ser | Lys | Arg | | | | | | | | | | | | | | |
| 320 |     |     | | | | | | | | | | | | | | | ctgtgataag gtgtggctag agcgatgcgt gtgagacggg tatgtcacgg tcgactggtc    1068
    tgatggccaa tggcatcggc catgtctggt catcacgggc tggttgcctg ggtgaaggtg    1128
    atgcacatca tcatgtgcgg ttggagggc tggcacagtg tgggctgaac tggagcagtt     1188
    gtccaggctg gcgttgaatc agtgagggtt tgtgattggc ggttgtgaag caatgactcc    1248
    gcccatattc tatttgtggg agctgagatg atggcatgct tgggatgtgc atggatcatg    1308
    gtagtgcagc aaactatatt cacctagggc tgttggtagg atcaggtgag gccttgcaca    1368
    ttgcatgatg tactcgtcat ggtgtgttgg tgagaggatg gatgtggatg gatgtgtatt    1428
    ctcagacgta gaccttgact ggaggcttga tcgagagagt gggccgtatt ctttgagagg    1488
    ggaggctcgt gccagaaatg gtgagtggat gactgtgacg ctgtacattg caggcaggtg    1548
    agatgcactg tctcgattgt aaaatacatt cagatgcaaa aaaaaaaaa aaaaaaaaa       1608

<210> SEQ ID NO 2
<211> LENGTH: 322
<212> TYPE: PRT
<213> ORGANISM: Haematococcus pluvialis

<400> SEQUENCE: 2

Thr Phe His Lys Pro Val Ser Gly Ala Ser Ala Leu Pro His Ile Gly

-continued

```
  1               5                  10                 15
Pro Pro Pro His Leu His Arg Ser Phe Ala Ala Thr Thr Met Leu Ser
             20                  25                 30
Lys Leu Gln Ser Ile Ser Val Lys Ala Arg Arg Val Glu Leu Ala Arg
             35                  40                 45
Asp Ile Thr Arg Pro Lys Val Cys Leu His Ala Gln Arg Cys Ser Leu
         50                  55                 60
Val Arg Leu Arg Val Ala Ala Pro Gln Thr Glu Glu Ala Leu Gly Thr
 65                  70                  75                 80
Val Gln Ala Ala Gly Ala Gly Asp Glu His Ser Ala Asp Val Ala Leu
             85                  90                 95
Gln Gln Leu Asp Arg Ala Ile Ala Glu Arg Arg Ala Arg Arg Lys Arg
             100                 105                110
Glu Gln Leu Ser Tyr Gln Ala Ala Ala Ile Ala Ala Ser Ile Gly Val
             115                 120                125
Ser Gly Ile Ala Ile Phe Ala Thr Tyr Leu Arg Phe Ala Met His Met
 130                 135                 140
Thr Val Gly Gly Ala Val Pro Trp Gly Glu Val Ala Gly Thr Leu Leu
145                  150                 155                160
Leu Val Val Gly Gly Ala Leu Gly Met Glu Met Tyr Ala Arg Tyr Ala
             165                 170                175
His Lys Ala Ile Trp His Glu Ser Pro Leu Gly Trp Leu Leu His Lys
             180                 185                190
Ser His His Thr Pro Arg Thr Gly Pro Phe Glu Ala Asn Asp Leu Phe
             195                 200                205
Ala Ile Ile Asn Gly Leu Pro Ala Met Leu Leu Cys Thr Phe Gly Phe
 210                 215                 220
Trp Leu Pro Asn Val Leu Gly Ala Ala Cys Phe Gly Ala Gly Leu Gly
225                  230                 235                240
Ile Thr Leu Tyr Gly Met Ala Tyr Met Phe Val His Asp Gly Leu Val
             245                 250                255
His Arg Arg Phe Pro Thr Gly Pro Ile Ala Gly Leu Pro Tyr Met Lys
             260                 265                270
Arg Leu Thr Val Ala His Gln Leu His His Ser Gly Lys Tyr Gly Gly
             275                 280                285
Ala Pro Trp Gly Met Phe Leu Gly Pro Gln Glu Leu Gln His Ile Pro
 290                 295                 300
Gly Ala Ala Glu Glu Val Glu Arg Leu Val Leu Glu Leu Asp Trp Ser
305                  310                 315                320
Lys Arg
```